United States Patent
Edwards et al.

(10) Patent No.: US 6,807,439 B2
(45) Date of Patent: Oct. 19, 2004

(54) SYSTEM AND METHOD FOR DETECTING DISLODGEMENT OF AN IMPLANTABLE MEDICAL DEVICE

(75) Inventors: Jerome Edwards, Superior, CO (US); William J. Flickinger, Lino Lakes, MN (US); Bradley A. Jascob, Broomfield, CO (US)

(73) Assignee: Medtronic, Inc., Minneapolis, MN (US)

( * ) Notice: Subject to any disclaimer, the term of this patent is extended or adjusted under 35 U.S.C. 154(b) by 572 days.

(21) Appl. No.: 09/824,953

(22) Filed: Apr. 3, 2001

(65) Prior Publication Data

US 2002/0161295 A1 Oct. 31, 2002

(51) Int. Cl.[7] ............................. A61B 5/05; A61N 1/18
(52) U.S. Cl. ......................................... 600/420; 607/28
(58) Field of Search .................. 600/420, 431, 600/433, 435, 436, 421, 422, 423, 509; 250/302; 424/9.3; 607/123, 4, 27, 28

(56) References Cited

U.S. PATENT DOCUMENTS

| | | | | |
|---|---|---|---|---|
| 4,154,247 A | | 5/1979 | O'Neill | 128/419 P |
| 4,402,329 A | | 9/1983 | Williams | 128/785 |
| 4,469,104 A | | 9/1984 | Peers-Trevarton | 128/419 P |
| 4,497,326 A | | 2/1985 | Curry | 128/785 |
| 4,640,285 A | * | 2/1987 | DeCote et al. | 607/27 |
| 5,018,530 A | * | 5/1991 | Rank et al. | 600/562 |
| 5,042,498 A | * | 8/1991 | Dukes | 600/509 |
| 5,628,778 A | | 5/1997 | Kruse et al. | 607/123 |
| 5,628,779 A | | 5/1997 | Bornzin et al. | 607/123 |
| 5,697,377 A | | 12/1997 | Wittkampf | 128/696 |
| 5,713,932 A | | 2/1998 | Gillberg et al. | 607/27 |
| 5,910,120 A | | 6/1999 | Kim et al. | 600/509 |
| 5,944,746 A | * | 8/1999 | Kroll | 607/27 |
| 6,067,469 A | * | 5/2000 | Kim et al. | 607/4 |
| 6,171,240 B1 | * | 1/2001 | Young et al. | 600/410 |
| 6,185,448 B1 | * | 2/2001 | Borovsky | 600/424 |
| 6,195,584 B1 | * | 2/2001 | Hill et al. | 607/28 |
| 6,484,050 B1 | * | 11/2002 | Carroll et al. | 600/436 |
| 6,490,486 B1 | * | 12/2002 | Bradley | 607/28 |

* cited by examiner

*Primary Examiner*—Daniel Robinson
(74) *Attorney, Agent, or Firm*—Girma Wolde-Michael; Daniel G. Chapik (57) ABSTRACT

An improved system and method for detecting dislodgement of an implantable medical device (IMD) such as a catheter or lead is disclosed. The system includes means for generating multiple, orthogonally-related signals within a body. For example, three current signals having a current path substantially oriented in the X, Y, and Z directions may be generated within the body. The invention further includes an IMD having an affixation device such as a helix at a distal tip for attachment to body tissue, and at least two sensing devices to sense the signals generated within the body. The difference in signal levels between two of the sensing devices may be measured. For example, a voltage potential difference created by the currents within the body may be measured between two electrodes. This measured signal level has components in the X, Y, and Z directions, and may therefore be used to define a directional vector in three-dimensional space. This vector is indicative of the orientation of the IMD. By comparing a directional vector indicative of a current IMD position with a vector indicative of a reference orientation, dislodgement of the IMD may be detected. In one embodiment, the reference orientation may be associated with a position wherein the IMD distal end is substantially perpendicular to the tissue. The comparison between the reference orientation and a subsequent IMD orientation may be performed by calculating the angle between the two associated vectors. If the angle exceeds a predetermined maximum angle, dislodgement is indicated.

28 Claims, 6 Drawing Sheets

SYSTEM AND METHOD FOR DETECTING DISLODGEMENT OF AN IMPLANTABLE MEDICAL DEVICE

FIELD OF THE INVENTION

The current invention relates to implantable lead or catheter systems; and more particularly, relates to a system and method for detecting when an implanted lead or catheter becomes dislodged from body tissue.

BACKGROUND OF THE INVENTION

Many modern medical therapies utilize internally-located leads or catheters implanted within the body either acutely or chronically to delivery therapy and/or to perform diagnosis. For example, cardiac pacemakers typically employ endocardial pacing leads that carry electrodes positioned within the atrial and/or ventricular chambers of the heart to deliver electrical stimulation to cardiac tissue. These leads may also be utilized to obtain an electrogram (EGM) waveform which is indicative of the electrical signals occurring within a patient's heart. Other types of leads carrying various types of sensors may be located within a patient's heart, vascular system, or at other locations within the body to obtain other physiological signals used in diagnosis and treatment of a patient. For example, leads carrying pressure, temperature, flow-rate, activity, and many other types of sensors may be located within the body to gather physiological data.

Some types of leads or catheters are located within a patient temporarily to perform measurements. For example, commonly-assigned U.S. Pat. No. 5,697,377 to Wittkampf incorporated herein by reference describes a system and method of determining the precise location of a medical device as that device is navigated through the vascular system of a patient's body. The disclosed navigation system, which may be utilized during mapping, surgical, or implant procedures, employs a reference catheter positioned at a predetermined, stationary position within the patient's body. The medical device, which may be a lead or catheter, carries a second electrode. The voltage potential difference existing between the reference electrode and the second electrode as described in terms of a three dimensional vector is utilized to determine the precise location of the medical device within the body. To obtain accurate location information, it is critical that the reference catheter be maintained at a stationary position in the body.

In any of the foregoing examples, it is generally considered important to maintain the lead or catheter at a predetermined location within a patient's body. For example, obtaining meaningful physiological measurements often depends on retaining an instrument at a desired location within a body. Similarly, use of reference leads or electrodes to obtain positional data as performed by the above-described navigational system also requires the ability to maintain the reference lead in a stationary position.

Many types of mechanisms have been developed to aid in retaining implantable devices such as catheters and leads at stationary positions within a body. For example, the body of a lead may be shaped to urge an electrode into contact with predetermined body tissue such as the wall of a vessel or the heart. Such "passive" fixation mechanisms are described in U.S. Pat. No. 4,154,247 issued to O'Neill, U.S. Pat. No. 5,628,778, issued to Kruse et al. and U.S. Pat. No. 5,628,779 issued to Bornzin et al. Other passive fixation mechanisms include the use of tines located on a distal portion of a lead. These tines engage the trabeculae of the heart's inner surface or the walls of a vessel to stabilize the lead at a predetermined location. Alternatively, "active" fixation mechanisms such as a barb or hook extending from the lead body may be used to engage body tissue and hold the lead in place. The fixation mechanism may also serve as a pacing electrode. For example, a helix may be used to affix a lead to body tissue and to also delivery electrical simulation to the tissue. Such leads are disclosed in U.S. Pat. No. 4,402,329 issued to Williams and to U.S. Pat. No. 4,497,326 issued to Curry.

Although many forms of active and passive fixation mechanisms are known, lead dislodgement remains a problem. For this reason, many systems have been developed to detect catheter or lead dislodgement. One approach to detection of dislocation is set forth in U.S. Pat. No. 5,713,932 issued to Gillberg et al. This patent discloses a cardiac stimulator in which a test pace pulse is delivered to the right atrium. If a ventricular depolarization occurs within a predetermined expected time interval after the pace pulse is delivered, the pace/sense electrode in the atrium is determined to be in contact with cardiac tissue.

According to another method of detecting lead dislodgement as disclosed in U.S. Pat. No. 5,944,746, a change in impedance measurements as measured between multiple electrodes positioned within a heart chamber are utilized to detect lead dislodgement. This mechanism, like the one discussed in the foregoing paragraph, has the disadvantage of requiring multiple electrodes positioned at various locations within the body. Such a configuration may not be available in some situations.

An alternative approach for detecting lead or catheter dislocation is disclosed in U.S. Pat. No. 6,067,469. According to this method, the various characteristics of an electrogram (EGM) are analyzed to determine whether lead dislodgement has occurred. More specifically, the signal levels occurring at the peak of the P and R waves are compared. If the R-wave peak value is a predetermined percentage of the P-wave peak value, lead dislodgement is indicated. This mechanism requires the capability to monitor and analyze an EGM signal. Not all systems include this type of capability.

While many of the existing mechanisms for detecting lead dislodgement are adapted for chronically-implanted lead systems coupled to implantable pulse generation systems, what is needed is an improved method for detecting lead dislodgement adapted for use with acutely-implanted lead or catheter systems not necessarily coupled to a pacing device. Ideally, the system is adapted for use with the type of navigational system described in the above-referenced patent to Wittkampf.

SUMMARY OF THE INVENTION

The system and method of the current invention provides an improved mechanism for detecting dislodgement of a distal end of an implantable medical device (IMD) such as a catheter or lead that is implanted within a body. The invention includes an IMD having an affixation device such as a helix at a distal tip. This IMD carries at least two sensing devices such as electrodes located on a portion of the IMD. Preferably, these sensing devices are located near the IMD distal end. The system further includes means for generating multiple signals within the body. In one embodiment, each of the multiple signals is associated with a respective one of the X, Y, or Z directions.

In use, two of the sensing devices carried by the IMD are used to sense the multiple signals that are generated within the body. The difference in signal levels existing between the sensing devices is determined. Because this difference in signal levels has components in the X, Y, and Z directions, this difference may be used to define a directional vector in three-dimensional space. The vector is indicative of the orientation of the IMD. More specifically, this vector substantially corresponds to the orientation of the longitudinal axis of the distal end of the IMD.

One embodiment of the invention includes means to generate three orthogonally-related current signals within body. These current signals result in a voltage potential difference being generated between points within the body. This voltage potential difference, which may be measured between two electrodes, has components in the X, Y, and Z directions. These components may be made distinguishable by providing currents that each have a respectively different frequency, or that are offset from one another by a phase shift, for example. The voltage potential difference signal that may be measured between the two sensing devices may be used to derive a vector indicative of the orientation of the IMD.

In another embodiment of the invention, three magnetic fields may be established having a substantially orthogonal relationship with respect to one another. A device for sensing the strength of the magnetic field such as a Hall effect device may be used to sense the components of a magnetic field in a manner similar to that discussed above. This allows a vector to be obtained that describes the orientation of the IMD.

The inventive system includes means to monitor the orientation of the IMD to detect lead dislodgement. According to one embodiment of the invention, a reference orientation of the IMD is selected. A reference vector associated with this reference orientation is calculated by measuring signal levels between two of the sensing devices in the manner discussed above. Preferably, the reference vector is obtained when the longitudinal axis of the IMD at the point of affixation to tissue is substantially perpendicular to the surface of the tissue.

After a reference vector is derived, subsequent movement of the IMD is monitored by deriving directional vectors associated with new orientations of the IMD. The IMD is considered to be dislodged when a vector associated with a new position of the IMD has a predetermined relationship to the reference vector. For example, in one embodiment, the IMD is considered dislodged when the angle between the reference vector and the newly-derived vector exceeds a predetermined maximum angle. This maximum angle may be selectable by a user so that the sensitivity of the system may be controlled. Selection of the smaller angle provides a system that more readily indicates lead displacement.

The system may include a display to allow a user to view the IMD using, for example, fluorovisible media located at the distal end of the IMD. This may be used to confirm lead dislodgement. The system may further include a user interface to allow a user to select the maximum angle of movement. In one embodiment, the user is further allowed to select the reference orientation of the IMD. An audible alarm may be provided to alert the user to lead dislodgement.

The system described in the fore-going paragraphs is particularly adapted for use with a navigation system of the type discussed in above-referenced U.S. Pat. No. 5,697,377 to Wittkampf. This navigation system tracks the movement of a second IMD as compared to a stationary reference IMD by measuring the difference in signal levels between a point on the second IMD and the reference IMD. This is accomplished using principles similar to those discussed above. The accuracy of this navigation system depends on the reference IMD maintaining a stationary position within a body. It is therefore important that any dislodgement of the reference IMD be detected immediately. This information is readily provided by the current inventive system.

DETAILED DESCRIPTION OF THE DRAWINGS

Figure 1:
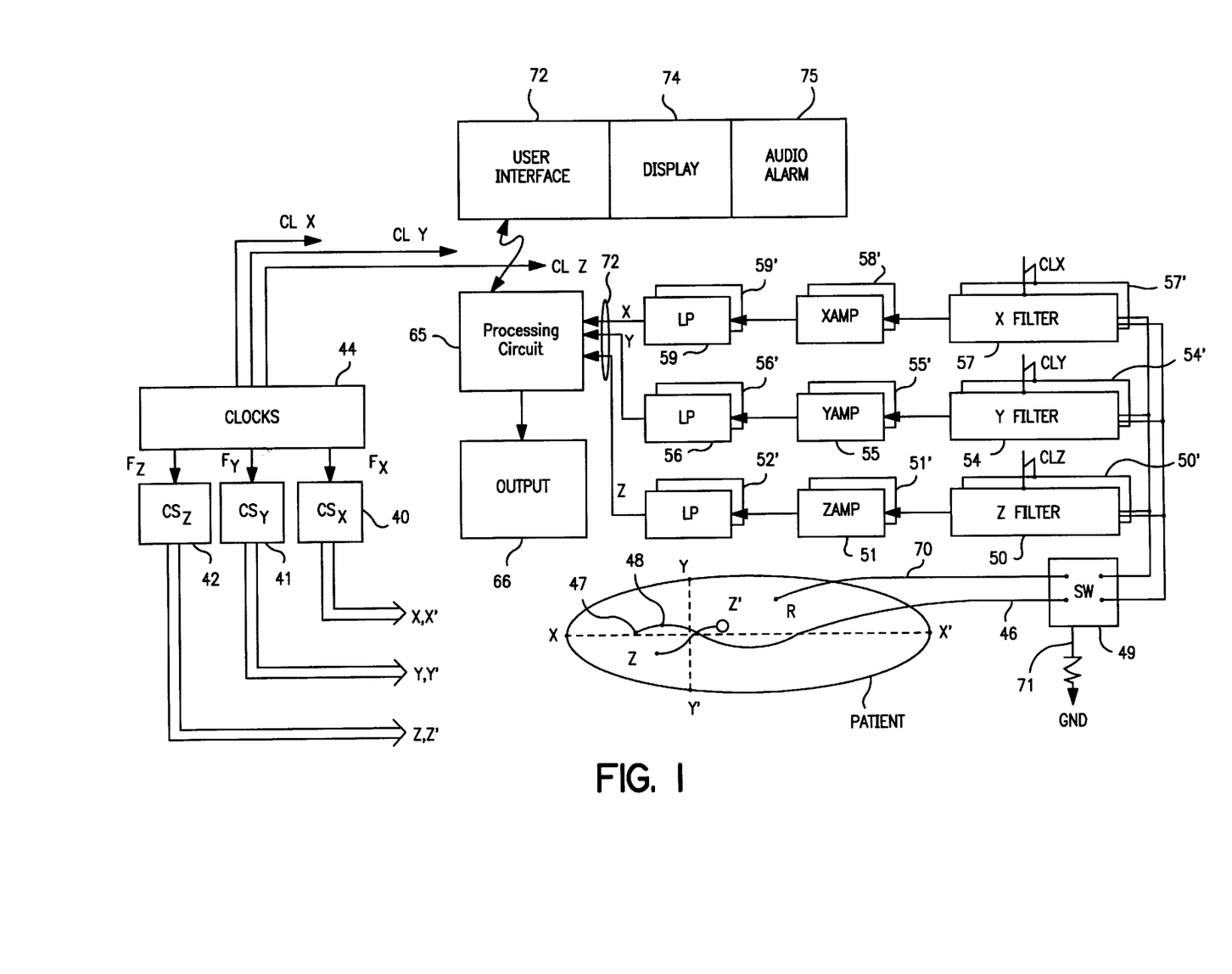
FIG. 1 is a block diagram illustrating the major components of the system of this invention as used for detection of lead dislodgement.

This invention is based upon using the patient, and in a specific embodiment example, the patient's heart, as a potentiometer in three orthogonal directions. This is described in commonly-assigned U.S. Pat. No. 5,697,377 to Wittkampf, which is incorporated herein by reference in its entirety. Orthogonal high-frequency current sources are utilized to transmit a relatively low current in each of three respective orthogonal directions through the patient, directed toward or near the body area of interest. As seen in FIG. 1, respective current sources 40, 41 and 42 are used to generate signals applied to electrodes which are shown diagrammatically as electrode pairs x, x'; y, y'; and z, z'. A catheter 46 is introduced into the patient, and for purposes of the ongoing discussion it will be assumed that the distal end of the catheter is introduced into the patient's heart. The catheter has at least two electrodes, illustrated as electrodes 47 and 48. Electrode 47 is at about the tip end of the catheter, and can be positioned at or adjacent to the heart wall area of interest. As used herein, the tip electrode may be actually at the tip, or displaced somewhat proximally from the tip but in the distal tip region of the catheter. The second electrode 48 is positioned a predetermined distance D from the electrode 47. Although only two such electrodes are shown, the catheter may contain three, four or more electrodes, so long as it contains at least a position detecting electrode, preferably at or near the tip, and further provides a pair of electrodes separated by a predetermined distance D, for calibration purposes as set forth below. Note that a PTCA catheter can have two electrodes near its tip, or on opposite sides of the balloon, with suitable connections for use in the practice of this invention.

In a first embodiment, the three electrical signals applied to the patient are high-frequency current signals, each provided at a slightly different frequency. For example, the current source which drives the x, x' electrodes, designated CSx, may operate at 30 kHz, with a current of about 0.1 mA. A second current source CSy may operate at 31 kHz, and the third current source CSz may operate at 32 kHz. In the alternative, all three sources can operate at about the same frequency, but are time multiplexed so that they can be distinguished upon subsequent pick-up of sensed signals. The important distinction is that some characteristic such as frequency, phase or time is adjusted for each of the three applied signals, so that three signals can be sensed in the patient and then separated out as respective x, y and z signals.

It is to be noted that the range of 25–50 kHz is advantageous for practice of this invention, because it is well above the usual upper cut off frequency of bandpass endocardial electrogram amplifiers. Lower frequencies may also be used, but in such case specially trimmed filters are required for all electrogram amplifiers to eliminate the external signals. If, however, the invention is practiced with procedures where no endocardial electrograms are recorded, e.g. PTCA, then the external source frequencies may be much lower. Likewise, the orthogonal signals may have any current level suitable for avoiding noise pickup in other signals. And while current pulses are preferred because they eliminate the influence of varying skin contact impedance, the signals may be voltage pulses in some applications. Thus, the optimum frequency, as well as the signal level, will depend upon the application.

Still referring to FIG. 1, and assuming three different frequency external signals, the mathematical basis for the inventive method of detecting lead dislodgement is explained. Tip electrode 47 and the second electrode 48 may be connected to three detection filters 50, 54, 57, each of which is adjusted to be sensitive to a respective one of the three current source frequencies. In another embodiment, these filters may be omitted, and the current provided directly to a respective signal amplifier. In either embodiment, a voltage is sensed between tip electrode 47 and second electrode for each orthogonal current. Presuming that the body behaves linearly, the voltage measured between the two electrodes has a component that corresponds with each of an x, y, and z axes. The voltages that correspond to the x, y, and z axes may be described, respectively as:

Vx=ax;

Vy=by; and

Vz=cz.

The constants, or sensitivities, a, b and c, are constant values expressed in mV/mm. These values may be determined using the circuitry shown in FIG. 1 as described in the following paragraphs.

System Calibration:

Two sets of equally sensitive detection amplifiers and signal processing paths are provided for each direction x, y, and z, as illustrated in FIG. 1. Each of the two electrodes 47 and 48 receives a voltage signal for each of the x, y and z currents. The following equations may be used to describe the voltage signals sensed by tip electrode 47:

$Vx_1=ax_1$, $Vy_1=by_1$, and $Vz_1=cz_1$

Similarly, the following equations may be used to describe the voltage signals sensed by the second electrode 48:

$Vx_2=ax_2$, $Vy_2=by_2$, and $Vz_2=cz_2$

To calculate the unknowns a, b and c, it is necessary to use the measured values:

$\Delta Vx=Vx_2-Vx_1$;

$\Delta Vy=Vy_2-Vy_1$; and $\Delta Vz=Vz_2-Vz_1$.

Additionally, the following equations are needed:

$\Delta x=x_2-x_1$;

$\Delta y=y_2-y_1$; and $\Delta z=z_2-z_1$.

Since $\Delta Vx=Vx_2-Vx_1$, then using substitution, $\Delta Vx=ax_1-ax_2$, or $\Delta Vx=a\Delta x$.

Similarly, $\Delta Vy=b\Delta y$; and $\Delta Vz=c\Delta z$.

Finally, using simple trigonometry, it is known that:

$\Delta x^2+\Delta y^2+\Delta z^2=D^2$, where D is the distance between the electrodes 47 and 48.

Using this information, and principles of substitution, the following is obtained:

$$\left(\frac{\Delta V_x}{a}\right)^2 + \left(\frac{\Delta V_y}{b}\right)^2 + \left(\frac{\Delta V_z}{c}\right)^2 = D^2$$

To simplify, the following substitutions may be made:

$1/a^2=A$;

$1/b^2=B$; and $1/c^2=C$.

Additionally, $\Delta V_x^2=X$;

$\Delta V_y^2=Y$; and $\Delta V_z^2=Z$.

This provides the following simplified equation:

$AX^2+BY^2+CZ^2=D^2$ where X, Y and Z are obtained from the measured voltage values at the electrodes 47 and 48, and D is the known inter-electrode distance. It is now required only to obtain measurements for three such equations, by placing the catheter in three different orientations, in the same heart chamber or other body area. This does not require any extra procedure, because the catheter in any event is being continuously manipulated within the heart during catheterization. Note that it is not necessary to obtain these three orientations separately at the beginning of the procedure. Indeed, earlier position data can be corrected with later obtained calibrations. When the three sets of orientation data are obtained, the three simultaneous equations can be solved for A, B and C, the calibration values of a, b and c can then be calculated. While theoretically there are always two solutions for a, b and c from A, B and C, only the positive solution is the correct one.

In practice, the system may not be ideally homogeneous, meaning that any given set of obtained measurements is not absolutely correct. This is not a basic problem to obtaining accurate measurements, since the calculations can be continuously performed automatically during catheterization, and the results can be averaged. Thus, as long as the catheter is being manipulated, the calibration measurements and calculations can be repeated any number of times, and a resulting average obtained that provides a very real and accurate position determination. Note also that it is easy with this invention to calculate the calibration constants, or sensitivities, for different areas of the heart chamber. This could be useful since the measurements may not be precisely linear. By recalculating the calibration constants for different areas of the heart chamber, calculated relative positions can be reliably obtained for clinical use in mapping and ablation purposes.

Even without any calibration, catheterization can be performed by assuming a "ballpark" sensitivity based, for example, on the weight or thorax dimensions of the patient. Note also that it is not usually necessary to map the whole heart chamber. Mapping is only necessary in a certain part or area of the chamber where the lead will be ultimately located.

In another embodiment of the invention, calibration can be achieved without using two electrodes in the heart, by assuming certain cardiac dimensions while only measuring $V_x$, $V_y$, and $V_z$ on the mapping electrode. For example, before entering the left ventricle, the catheter has to be manipulated through the aorta descendens, the aortic arc, and the aortic valve. With the patient on his or her back, the depth from the aorta descendens to the aortic valve is approximately 5 cm. The distance from the aortic valve to the left ventricular apex is known to be close to 10 cm. Using such approximate distance figures, together with the measured voltages at those sites, it is possible to generate a sensitivity calibration when the system is "told" where, in an anatomical sense, the catheter electrodes are positioned. This results in catheter positions inside a normalized left ventricle. The same technique can be used in other heart chambers for obtaining reliable position data.

Use of the Current Invention to Detect Lead Dislodgement

A.—Defining an Allowable Range of Movement for the Catheter

The system and method described above may be used in one embodiment of the invention to perform calibration. After calibration is completed, the system may be used to detect catheter dislodgement in a manner described in the following paragraphs.

Figure 2:
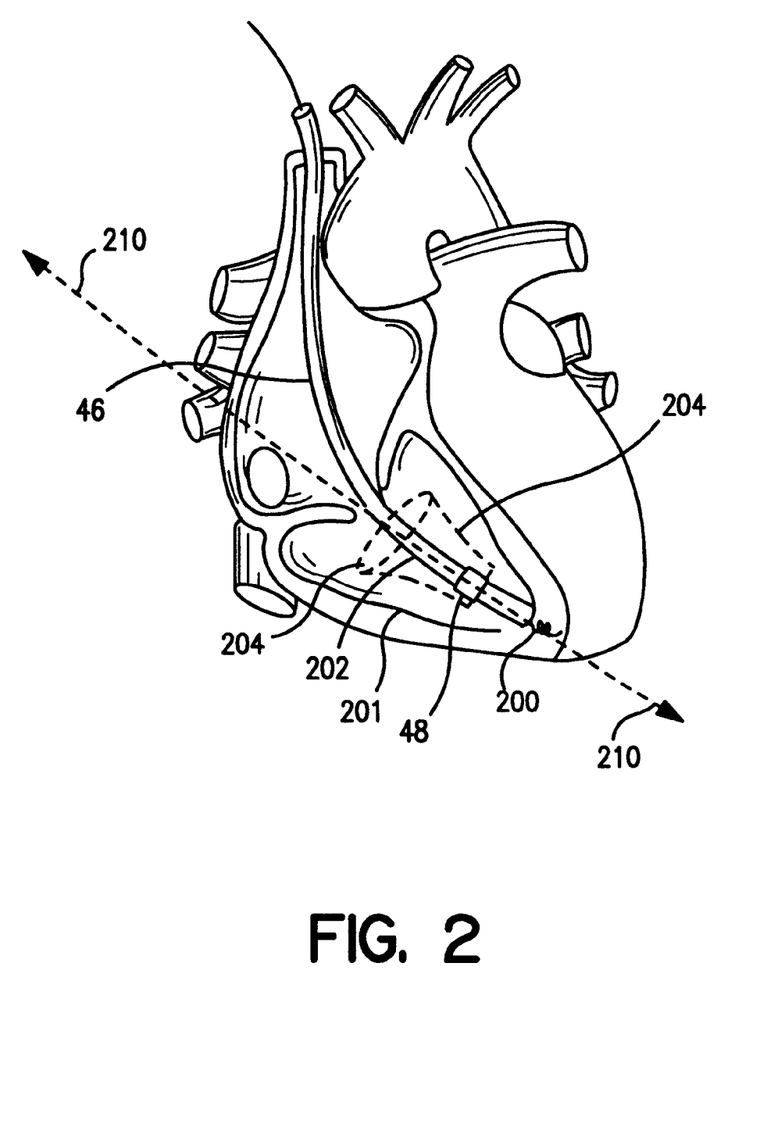
FIG. 2 is a diagram illustrating the catheter positioned within the right ventricle of the heart, and further illustrates an allowable region of movement for the catheter.

FIG. 2 illustrates catheter 46 of FIG. 1 located at a predetermined location within a patient's right ventricle 201. According to the current invention, the distal tip of catheter 46 includes an active fixation member 200 such as a fixation helix to affix the distal tip of the catheter to myocardial tissue. The portion 202 of catheter 46 that is proximal to the fixation member 200 is free to move somewhat as the heart beats, and as the patient moves. However, as long as the distal tip of catheter 46 remains affixed to the myocardial tissue, any movement in the catheter body will be maintained in essentially a conical region defined by dashed lines 204. If the distal tip of the catheter exhibits an orientation that exits the conical region, it is likely dislodgement has occurred.

Before the system can be used to detect dislodgement, a reference position of the catheter must be obtained. This reference position is obtained after the catheter distal tip is affixed to myocardial tissue using helix 200. When the distal tip of the catheter is essentially perpendicular to the myocardial tissue, the reference vector that coincides generally with line 210 of FIG. 2 may be determined using x, y, and z Cartesian coordinates as discussed in the following paragraphs.

Recall that the circuit of FIG. 1 is capable of measuring the various x, y, and z signal components for a signal measured at electrodes 47 and 48. In FIG. 2, assume that helix 200 is an electrode, and similar signal measurements may be obtained at helix 200 and electrode 48. These signal measurements may be described as follows:

$Vx_1=ax_1$, $Vy_1=by_1$, and $Vz_1=cz_1$; and $Vx_2=ax_2$, $Vy_2=by_2$, and $Vz_2=cz_2$.

From these measurements, a potential difference signal described in terms of the voltage values $\Delta Vx$, $\Delta Vy$, and $\Delta Vz$ may be generated in the manner described above. These values correspond to x, y, and z directional values as discussed above, and as set forth as follows:

$\Delta Vx=a\Delta x$;

$\Delta Vy=b\Delta y$; and $\Delta Vz=c\Delta z$.

The values for $\Delta Vx$, $\Delta Vy$, and $\Delta Vz$ are provided to processing circuit 65 on lines 72. In a manner known in the art, processing circuit 65 may include hardware circuits executing any combination of software and/or firmware instructions. Since the values a, b, and c are now known, processing circuit may calculate the values for $\Delta x$, $\Delta y$, and $\Delta z$. These values define a vector in three-dimensional space.

At any desired moment in time, the system of FIG. 1 may be used to measure a three-dimensional vector indicative of the orientation of the distal tip of catheter 46. A user may utilize an interface such as a user interface 70 (FIG. 1) to indicate when the reference vector should be measured. User interface 70 could be any type of interface such as a touch screen, key board, mouse, or any other type of interface device that is coupled to, or otherwise in communication with, processing circuit 65. Generally, the user will select a reference vector corresponding to the catheter distal tip being oriented substantially perpendicular to body tissue at the point where the catheter is affixed to the body tissue.

After defining the reference vector, the catheter is allowed to move within the body. As the catheter moves into a different position, a new vector describing the orientation of the distal tip may be calculated using the steps discussed above. An angle will exist between the reference vector and the new vector indicative of the new catheter position. If the absolute value of this angle is greater than the predetermined allowable angle defined by the apex of conical region 204, dislodgement is indicated. This is described in more detail in reference to FIG. 3.

Figure 3:
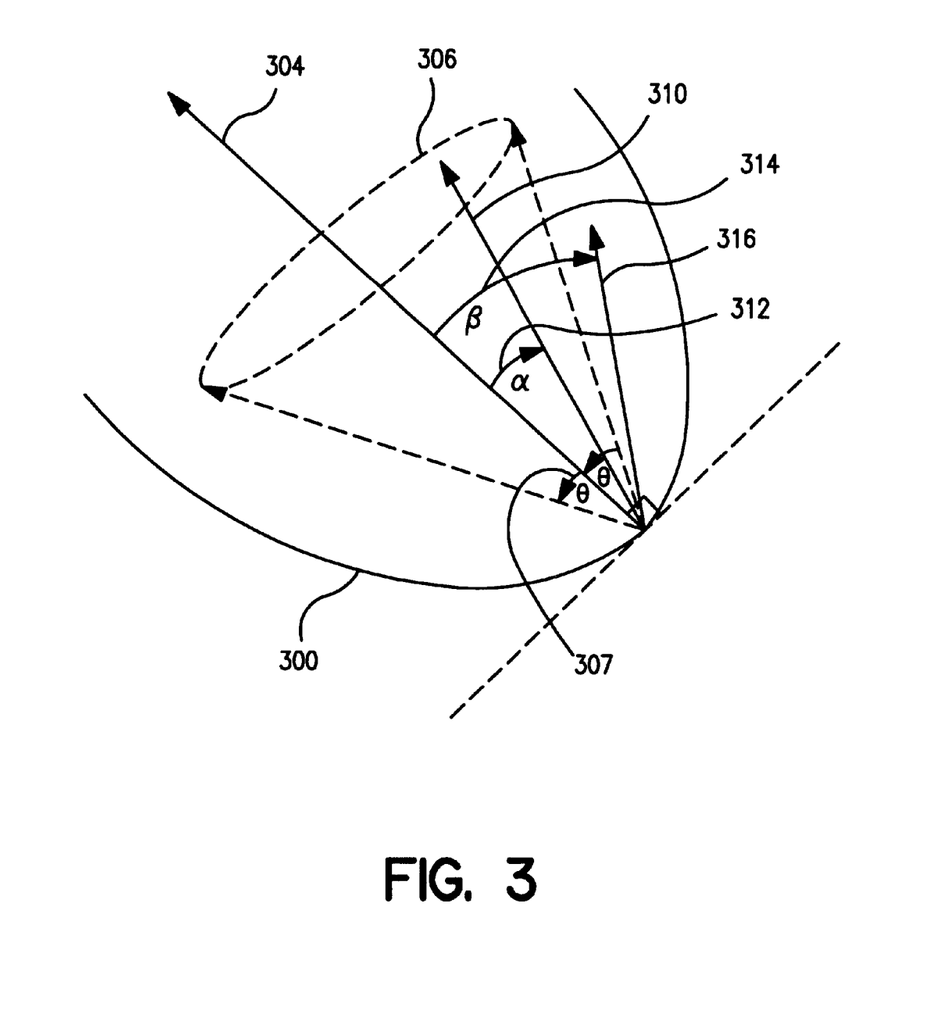
FIG. 3 is a diagram illustrating movement of the catheter distal tip from the reference position to a new position when the catheter is affixed to tissue within a heart chamber.

FIG. 3 is a diagram illustrating movement of the catheter distal tip from the reference position to a new position when the catheter is affixed to tissue within heart chamber 300. As user selects the catheter reference position represented by line 304 when the catheter distal tip is essentially perpendicular to the surface of the heart chamber 300 at the point of contact. Dashed lines 306 correspond to the allowed region of movement of the catheter from this reference position. As shown, the catheter orientation can change from the reference position by as much as an angle of θ 307 in any direction and still be within the allowed range of movement. It may be noted that this range of motion occurs in three-dimensional space. Angle θ may therefore exist in any direction in three-dimensional space as compared to the reference vector.

FIG. 3 further shows an exemplary new orientation for the catheter having a vector represented by line 310. The angle α 312 exists between the reference vector represented by line 304 and the longitudinal axis of the catheter distal tip at the new position, as represented by line 310. Since the absolute value of α is less than, or equal to, the angle θ, no catheter dislodgement is indicated. That is, no catheter dislodgement is detected when $|\alpha| \leq \theta$.

Next, assume the angle between the reference vector and the vector representing the longitudinal axis of the catheter at the new position increases to angle β 314, as represented by line 316. In this situation, $|\beta| > \theta$, and catheter dislodgement will therefore be indicated.

Figure 4:
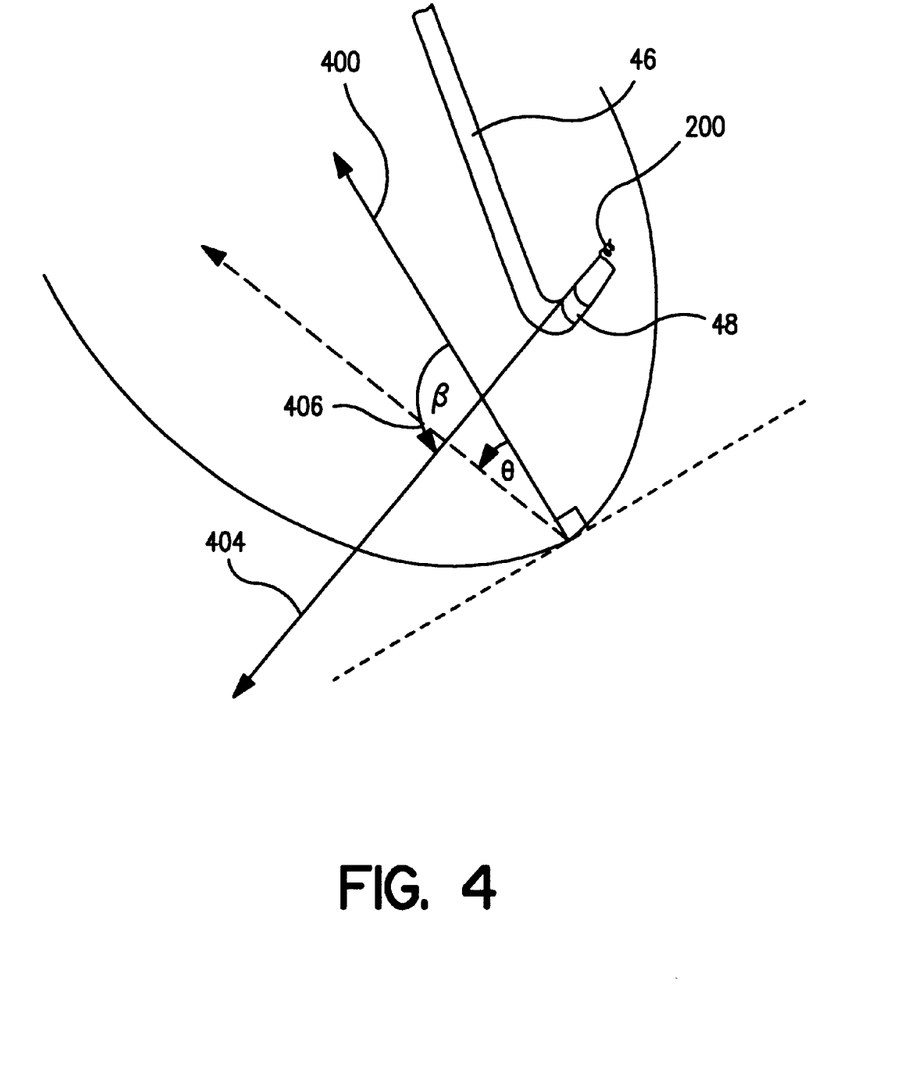
FIG. 4 is a diagram of catheter inside a cardiac chamber, and illustrates the manner in which the current system operates in practice.

FIG. 4 is a diagram of catheter 46 inside a cardiac chamber, and illustrates the manner in which the current system operates in practice. Line 400 represents the reference vector position. The vector corresponding to the distal tip of the dislodged catheter is represented by Line 404. The intersection of line 404 and reference vector defines angle β 406. This angle is greater than angle θ defining the allowable range of motion, and therefore dislodgement is indicated.

Figure 5:
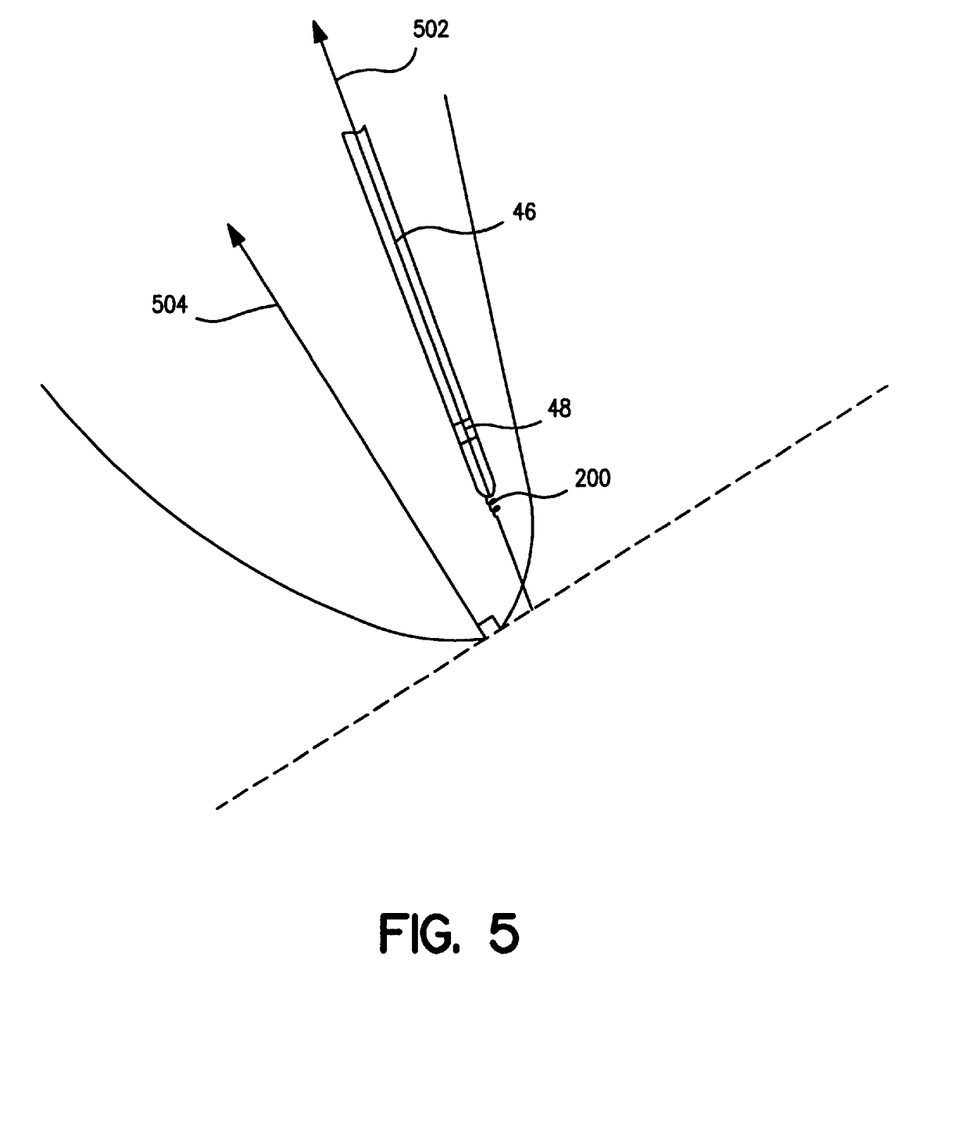
FIG. 5 is a diagram of catheter inside a cardiac chamber, and illustrates a second example of dislodgement.

FIG. 5 is a diagram of catheter 46 inside a cardiac chamber, and illustrates a second example of dislodgement. Catheter 46 is shown in a position such that the vector describing distal tip orientation, as represented by line 502, is essentially parallel to the line 504 corresponding to the reference vector. In this instance, the difference between the reference vector and the vector representing catheter position approaches zero, and no dislodgement is detected. Although this failure to detect lead dislodgement is theoretically possible, tests have shown that a dislodged lead distal tip experiences forces that cause the distal tip to twist and turn in a manner that makes this situation extremely unlikely. Once dislodgement occurs, the catheter tip is moving within the heart in a manner that is almost certain to cause the vector indicative of distal tip orientation to exit the allowable region of motion within a short time period.

In one embodiment, user interface 72 (FIG. 1) includes a display 74 to allow the user to view the movement of the distal tip of catheter 46 in three-dimensional space. This further allows the user to confirm that the distal tip had become dislodged. In yet a further embodiment, an audible alarm 75 (FIG. 1) may be provided to indicate that lead dislodgement has been detected.

In one embodiment, user interface 72 may be utilized to specify the reference position of the catheter 46. Recall that the reference position is generally selected when the longitudinal axis of the catheter distal tip is substantially perpendicular to the myocardial tissue at the location where the distal tip contacts the tissue.

The embodiment of the invention discussed above requires a calibration method to determine the values of a, b, and c, which are sensitivity factors expressed in mV/mm. These sensitivity values are used to determine the x, y, and z vector components from the voltage signal readings obtained from the electrodes. In one embodiment of the invention, this calibration of the system may not be needed. This is the case when the values for a, b, and c are all approximately the same, as may occur when the distance between the electrodes on the lead is small, or when the impedance of the body fluid between the two electrodes is substantially uniform around the area of the electrodes. In this instance, the voltage change values ΔVx, ΔVy, and ΔVz may be used instead of Δx, Δy, and Δz to determine the three-dimensional vector used to identify lead dislodgement. This eliminates the need to perform calibration, and reduces the amount of computation that is required after the voltage signals are measured.

It may further be noted that in the above description, the voltage values ΔVx, ΔVy, and ΔVz are described as being the difference between respective voltage components obtained at two electrodes. These measurements may be performed by considering one of the electrodes to be at a reference voltage level of 0 in all directions. The voltage values obtained at the second electrode may then be used for ΔVx, ΔVy, and ΔVz values. In an alternative embodiment, the voltage differences ΔVx, ΔVy, and ΔVz may be obtained by measuring the x, y, and z components of the voltage signal between a first electrode and a reference point such as a grounded point 71 shown on the system of FIG. 1. This process may be repeated for a second electrode. The voltage differences ΔVx, ΔVy, and ΔVz may then be calculated as the difference between respective voltage components of the first and second set of measurements.

Figure 6:
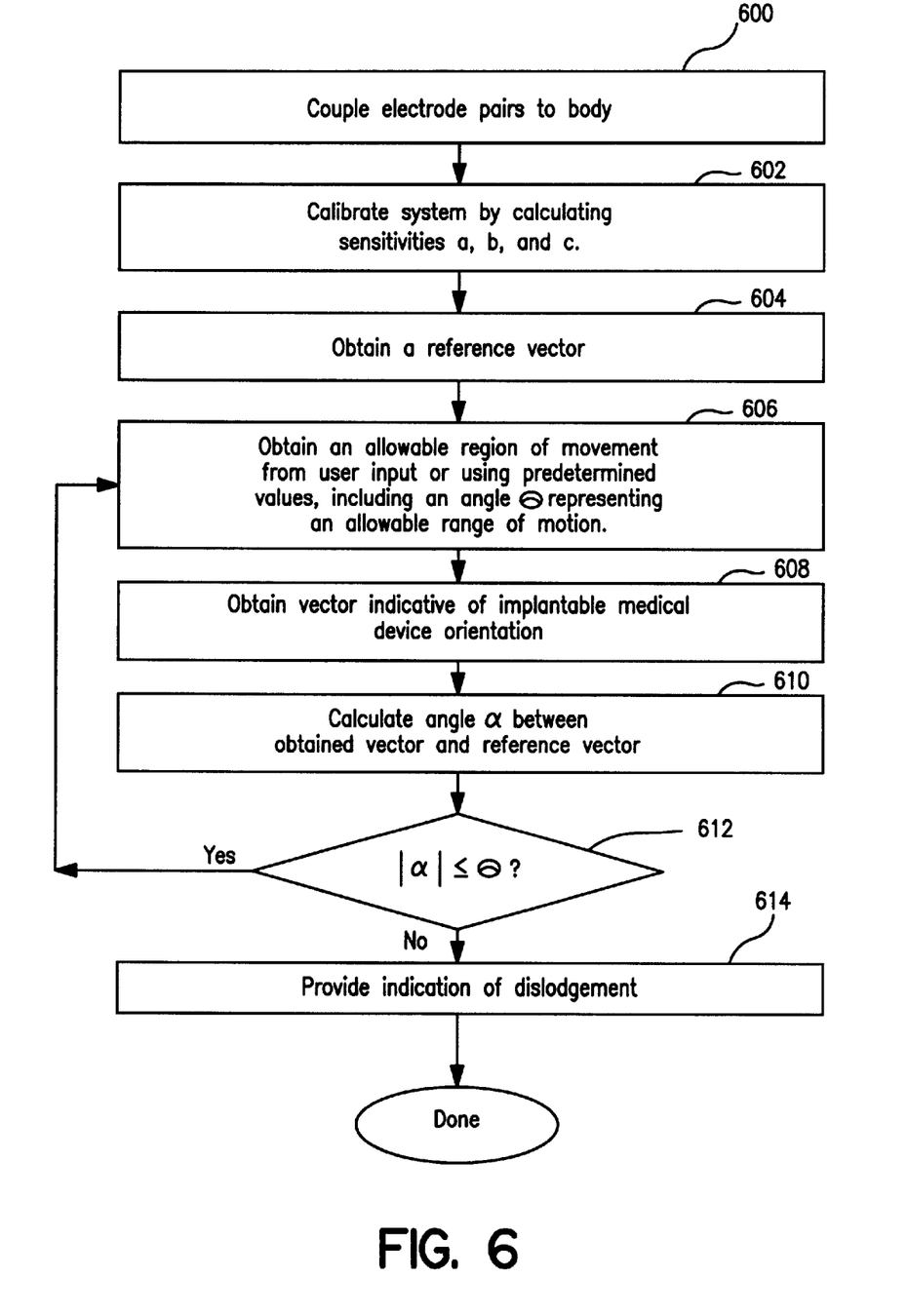
FIG. 6 is a flowchart illustrating the operation of the current invention.

FIG. 6 is a flow-chart indicating the method of detecting lead dislodgement according to the current invention. In step 600, three electrode pairs are connected to a patient in the manner described above so that a measurable potential difference signal is available along an X, Y, and Z axis. Step 602 illustrates calibration of the system to determine sensitivity values a, b, and c in a manner discussed above. Next, a reference vector location is obtained in step 604. This is performed when the catheter distal tip is affixed to tissue such as a myocardial wall, and is essentially perpendicular to the plane of the tissue at the point of contact.

After a reference vector is obtained, an allowable region of movement is defined, as depicted in step 606. This may be defined by selecting the angle θ, as described above. In one embodiment of the invention, this angle is pre-selected by the system. For example, an angle of 30° may be selected. In another embodiment, the user is allowed to specify the angle using user interface 70. In this instance, the angle may change depending on the type of implantable device being monitored. For example, if a device having a more flexible body is being monitored for dislodgement, a larger angle of allowed movement may be selected by the user. Specifying a smaller angle increases the sensitivity of the system so that lead dislodgement is indicated more often.

Next, the distal tip of the implantable medical device such as the catheter is monitored as shown in step 608. In one embodiment of the invention, this involves obtaining a vector indicative of distal tip orientation at predetermined time intervals. Each obtained vector is compared to the reference vector to determine the angle α is defined between the two vectors in three-dimensional space. This is illustrated in step 610. In decision step 612, it is determined whether $|\alpha| \leq \theta$. If so, no lead dislodgment is indicated, and the monitoring continues with step 606. However, if α is larger than θ, lead dislodgement is indicated to the user as shown in step 614. This may be accomplished, for example, user a warning on display 74, or using some other indication provided by user interface 72. For instance, an audible signal may also be generated for this purpose.

The above-described system may take the form of alternative embodiments. For example, assuming the constants a, b, and c are roughly the same, no calibration is necessary.

As noted above, the current system is particularly adapted for use with the navigational system described in U.S. Pat. No. 5,697,377 referenced above. The system is used to determine the precise location of an implantable medical device such a catheter 70 (FIG. 1) located within a body. The implantable medical device 70 carries at least one electrode. The voltage potential difference existing between this electrode and one of the electrodes 47 or 48 of catheter 46 is obtained in terms of a three dimensional vector. This is performed using techniques similar to those discussed above and described in detail in the '377 patent incorporated herein by reference. The three dimensional vector is utilized to determine the precise location of the implantable medical device 70 within the body. To obtain accurate location information, it is critical that the reference catheter 46 be maintained at a stationary position in the body. The current invention may be utilized to detect dislodgement of the reference catheter so that precise measurements are obtained.

Although the current system and method is adapted for use with the particular navigational system of the '377 patent, it may be utilized to detect dislodgement of any lead or catheter positioned anywhere in the body. Because the system requires the presence of measurable signals corresponding to the X, Y, and Z axis, the current system is generally adapted for use in monitoring for the dislodgement of acutely implanted devices.

It may further be noted that although the above-described system discusses the use of potential difference signals to determine a directional vector between two electrodes, other types of signals may be measured in a similar manner. For example, an electromagnetic field may be established in each of the X, Y, and Z directions. Two sensors adapted to measure electromagnetic field strength may be carried at a first and second location, respectively, on a distal end of an implantable medical device. The difference in field strength at the first and second locations may be used to derive a directional vector indicative of the orientation of the distal end in the manner discussed above. Ones skilled in the art will appreciate that other signals may be used for this purpose.

According to yet another aspect of the invention, more than two electrodes may be carried on the IMD and used to obtain multiple directional vectors. The multiple vectors may be used to obtain a more accurate representation of the orientation of the IMD such as by averaging one or more of the vectors, or otherwise processing the vectors to minimize errors.

Additional scopes and aspects of the invention will be apparent to those skilled in the art from the foregoing description and the accompanying drawings.

What is claimed is:

1. A system for detecting dislodgement of a first implantable medical device (IMD) affixed to body tissue at an elongated distal end of the first IMD, the system comprising:
   first and second sensing devices carried on the elongated distal end;
   a sensing circuit to obtain first and second signal measurements via the first and second sensing devices, respectively, and to further obtain a difference between the first and second signal measurements, wherein the difference is indicative of an orientation of the IMD; and
   a processing circuit to determine an allowable region of movement associated with the elongated distal end, and to further determine, at once, whether the orientation of the IMD is indicative of dislodgement of the elongated distal end.

2. The system of claim 1, and further including a user interface coupled to the processing circuit to receive user-specified data, and wherein the processing circuit is adapted to determine the allowable region of movement from the user-specified data.

3. The system of claim 2, wherein the user-specified data includes an allowable angle of motion.

4. The system of claim 3, wherein the sensing circuit includes means for sensing a reference signal indicative of a reference orientation of the elongated distal end, and wherein the processing circuit determines the allowable region of movement as compared to the reference orientation.

5. The system of claim 4, wherein the user interface is adapted to receive a signal from a user indicating when the reference signal should be obtained.

6. The system of claim 4, wherein the user interface is adapted to receive an indication of a maximum angle, and wherein the processing circuit includes means for defining the allowable region as that region wherein an angle between a longitudinal axis of the IMD and the reference orientation has a predetermined relationship to the maximum angle.

7. The system of claim 6, wherein the processing circuit includes means for defining the allowable region as that region wherein an angle between a longitudinal axis of the IMD and the reference orientation is less than the maximum angle.

8. The system of claim 1, and further including signal means for generating three substantially orthogonal signals in the tissue.

9. The system of claim 8, wherein the signal means includes means for generating three substantially orthogonal alternating current signals in the tissue.

10. The system of claim 9, wherein the first and second sensing devices are electrodes.

11. The system of claim 10, wherein the sensing circuit includes a circuit to measure a voltage potential difference that exists between the first and second sensing devices.

12. The system of claim 2, wherein the user interface includes a display to provide a three-dimensional representation of the location of the distal end of the IMD.

13. The system of claim 1, wherein the processing circuit includes calibration means for determining calibration factors associated with the first and second signal measurements.

14. The system of claim 13, wherein the calibration means generates sensitivity values associated with a three-dimensional vector.

15. The system of claim 1, wherein the system further includes a second IMD carrying a third sensing device to detect a third signal measurement, and wherein the processing circuit includes means to utilize ones of the first, second, and third signal measurements to obtain directional data indicative of the position of the second IMD.

16. A method for detecting dislodgement of an IMD within a body, the IMD having a distal end carrying first and second signal sensing devices and wherein the distal end is adapted to be affixed to body tissue, the method comprising the steps of:
   a.) determining a reference orientation of the IMD when the distal end is affixed to body tissue;
   b.) obtaining a first measurement of one or more signal levels existing at the first signal sensing device;
   c.) obtaining a second measurement of one or more signal levels existing at the second signal sensing device;
   d.) calculating a difference between the first and second measurements;
   e.) utilizing the calculated difference to determine a directional vector indicative of a second orientation of the distal end of the IMD; and
   f.) comparing the reference orientation and the second orientation to determine likelihood of lead dislodgement.

17. The method of claim 16, wherein the one or more signal levels include a voltage potential, and wherein method d.) includes the methods of obtaining a voltage potential difference between the first and second signal sensing devices.

18. The method of claim 16, wherein the one or more signal levels include one or more magnetic fields, and wherein step d.) includes the method of calculating a difference between the magnetic field strength at the first signal sensing device and the magnetic field strength at the second signal sensing device.

19. The method of claim 16, wherein method a.) includes the method of allowing a user to select the reference orientation.

20. The method of claim 16, wherein method a.) includes the method of selecting the reference orientation as the orientation wherein the distal end is substantially perpendicular to the body tissue at the point the IMD is affixed to the body tissue.

21. The method of claim 17, wherein method b.) includes the methods of:
- obtaining the first measurement of a voltage potential difference between a reference voltage point and the first signal sensing device;
- obtaining the second measurement of a voltage potential difference between a reference voltage point and the second signal sensing device; and
- calculating the difference between the first measurement and the second measurements to obtain the voltage potential difference existing between the first and second signal sensing devices.

22. The method of claim 16, wherein method b.) includes the method of obtaining components indicative of a point in three-dimensional space for each of the first and second measurements.

23. The method of claim 16, wherein method e.) includes the method of calculating sensitivity values for the one or more signal levels.

24. The method of claim 16, wherein method b.) includes the method of generating three substantially orthogonal signals in the body tissue.

25. The method of claim 24, wherein method b.) includes generating three substantially orthogonal alternating current signals in the body tissue.

26. The method of claim 16, and further including the method of providing a visual image of the second orientation of the distal end of the IMD.

27. The method of claim 16, and further including the method of providing an audio signal indicative of the detected lead dislodgement.

28. The method of claim 16, and further including the methods of
- providing a second IMD in the body, the second IMD having a third sensing device;
- obtaining a third measurement of one or more signal levels existing at the third signal sensing device; and
- utilizing ones of the first, second, and third measurements to determine the location of the third sensing device within the body.

* * * * *